(12) United States Patent
Hannes et al.

(10) Patent No.: US 9,034,026 B2
(45) Date of Patent: May 19, 2015

(54) IMPLANT FOR INFLUENCING BLOOD FLOW

(75) Inventors: Ralf Hannes, Dortmund (DE); Hermann Monstadt, Bochum (DE); Manuel Salen, Bochum (DE)

(73) Assignee: phenox GmbH, Bochum (DE)

( * ) Notice: Subject to any disclaimer, the term of this patent is extended or adjusted under 35 U.S.C. 154(b) by 144 days.

(21) Appl. No.: 12/529,983

(22) PCT Filed: Mar. 5, 2008

(86) PCT No.: PCT/EP2008/001740
§ 371 (c)(1),
(2), (4) Date: Feb. 9, 2010

(87) PCT Pub. No.: WO2008/107172
PCT Pub. Date: Sep. 12, 2008

(65) Prior Publication Data
US 2010/0152834 A1  Jun. 17, 2010

(30) Foreign Application Priority Data

Mar. 6, 2007  (DE) .......................... 10 2007 011 219
Mar. 14, 2007  (DE) .......................... 10 2007 012 964

(51) Int. Cl.
*A61F 2/82*  (2013.01)
*A61F 2/966*  (2013.01)
*A61F 2/90*  (2013.01)
*A61F 2/95*  (2013.01)

(52) U.S. Cl.
CPC .............. *A61F 2/90* (2013.01); *A61F 2002/823* (2013.01); *A61F 2002/9505* (2013.01); *A61F 2250/0015* (2013.01); *A61F 2250/0039* (2013.01)

(58) Field of Classification Search
CPC ..... A61F 2/90; A61F 2/95; A61F 2002/9505; A61F 2002/9528; A61F 2002/9534
USPC .................. 623/1.11–1.54; 606/108, 191–200
See application file for complete search history.

(56) References Cited

U.S. PATENT DOCUMENTS

| | | | |
|---|---|---|---|
| 4,441,215 A * | 4/1984 | Kaster | 623/1.53 |
| 4,655,771 A * | 4/1987 | Wallsten | 623/1.22 |
| 4,830,003 A * | 5/1989 | Wolff et al. | 606/191 |
| 5,443,496 A * | 8/1995 | Schwartz et al. | 623/1.16 |
| 5,591,172 A * | 1/1997 | Bachmann et al. | 623/1.11 |
| 5,709,713 A * | 1/1998 | Evans et al. | 623/1.53 |
| 5,824,041 A * | 10/1998 | Lenker et al. | 606/195 |
| 5,849,037 A * | 12/1998 | Frid | 623/1.2 |
| 6,083,257 A * | 7/2000 | Taylor et al. | 623/1.46 |
| 6,325,822 B1 * | 12/2001 | Chouinard et al. | 623/1.15 |
| 6,626,926 B2 * | 9/2003 | Friedman et al. | 606/169 |
| 6,626,936 B2 * | 9/2003 | Stinson | 623/1.15 |
| 6,652,582 B1 * | 11/2003 | Stinson | 623/1.39 |
| 6,989,024 B2 * | 1/2006 | Hebert et al. | 623/1.11 |
| 7,473,271 B2 * | 1/2009 | Gunderson | 623/1.12 |
| 7,771,463 B2 * | 8/2010 | Ton et al. | 623/1.11 |
| 7,993,387 B2 * | 8/2011 | Clerc et al. | 623/1.15 |
| 2005/0256563 A1 * | 11/2005 | Clerc et al. | 623/1.16 |

* cited by examiner

*Primary Examiner* — Kathleen Holwerda
(74) *Attorney, Agent, or Firm* — Berliner & Associates

(57) ABSTRACT

An implant for blood vessels, in particular to influence the flow of blood in the area of arteriovenous malformations. The implant has a wall comprising individual filaments combined so as to form a circular braiding, the circular braiding being positioned in elongated form and with a reduced diameter in an insertion catheter and expanding at the placement site thus adapting to the vessel diameter and increasing its braiding density.

21 Claims, 6 Drawing Sheets

IMPLANT FOR INFLUENCING BLOOD FLOW

BACKGROUND

1. Field of the Invention

The invention relates to an implant for blood vessels that has a wall comprising individual filaments combined to form a circular braiding. The implant shall in particular serve to influence the flow of blood in the area of arteriovenous malformations, for example fistulas and aneurysms. It may also be used in the treatment of ischemic strokes, for example to restore, increase or maintain the blood flow. The implant may be designed so as to be recoverable.

2. Related Art

Arteriovenous malformation may significantly impair a patient and may even result in fatal risks. In particular, this applies to arteriovenous fistulas and aneurysms, especially when these are found to exist in the cerebral region. Normally, attempts are made to close off such malformations by implants which, as a rule, are placed in position by endovascular techniques with the help of catheters.

Especially when treating aneurysms implanting platinum spirals has proven its worth, said spirals fill the aneurysm more or less completely, largely obstruct the blood inflow and enable a local thrombus or clot to form which fills and ultimately closes off the aneurysm. Nevertheless, this treatment approach only suits aneurysms that have a relatively narrow access to the vessel system, so-called aciniform aneurysms. In the event of vessel protuberances having a wide access to the blood vessel there is a risk that the implanted spirals may be flushed out and cause damage to other areas of the vascular system.

In such cases it has already been proposed to place a kind of stent into position that "bars" the opening of the aneurysm and in this way prevents occlusion spirals from being flushed out. Stents of this nature that are provided with a wide-meshed wall have certain drawbacks, however.

On the one hand, this concerns the wide-meshed structure which does not prevent blood from entering the aneurysm. So if the occlusion means does not occupy the aneurysm space adequately the pressure exerted on the vessel wall remains undiminished. An after-treatment in this case may be difficult, however, because the stent will obstruct access to the aneurysm and impair the placement of additional occlusion means.

Another drawback is that the stent cannot be adapted to its placement site. In the interest of functioning optimally the stent should have close contact with the vessel wall but not exert excessive pressure on the wall. Other than stents serving the purpose of expanding vessels to counteract stenoses this type of stent must rather be viewed as a kind of sleeve the influence of which on the vessel lumen and endothelium wall of the vessel shall be as slight as possible. It thus follows that this type of stent is only of limited use when it comes to meet the requirements in question even if it has been selected especially for the envisaged purpose.

Stents consisting of wire braiding are known for a long time, particularly for applications in the coronary area. These stents are usually manufactured as a round braiding structure with the individual wire filaments forming the stent wall in layers of oppositely running spirally or helically shaped elements. In this way a mesh braiding is produced that both supports in radial direction and is permeable to blood.

A problem encountered with these stents of circular braiding design is that the small-diameter loose ends existing on the free ends may have traumatic effects.

As proposed by U.S. Pat. No. 4,655,771 (Wallsten) such a stent of circular braiding is provided with U-shaped connecting links arranged between the loose ends which makes it atraumatic. However, the U-shaped connecting links are prone to cause stresses and thus lead to deformation of the stent.

As per U.S. Pat. No. 5,061,275 (Wallsten et al.) the loose ends of such wire stents are rounded off by laser treatment to counteract traumatization. The stent proposed in that publication also consists of circular braiding the individual wires of which are provided with impressions in the knots area so as to enable a stress-free fixation within the wall structure.

Such stents of circular braiding design consisting of filaments are, when used for the treatment of stenoses, expanded hydraulically by means of balloons at the placement site and attached to the vessel wall. During placement the balloon attached to a guide wire serves as transportation element over which the stent is crimp-mounted. However, such a transportation element should not be used for implants intended to influence or channel the flow of blood in the cerebral region; on the contrary, an implant automatically adapting to the vessel diameter and leaning against the vessel wall would be of advantage in this case.

Another problematic aspect associated with stents or implants made of wire braiding is their manufacture. Manufacturing them in the form of a braided endless hosing cut off to the desired length is viewed beneficial. In this case loose wire ends are produced at the two ends of the cut-to-size hosing which must be made blunt at great expense, for example by providing for the attachment of the above mentioned connecting links.

BRIEF SUMMARY

Accordingly, the objective of the present invention is to propose an implant capable of influencing the flow of blood in a vessel in such a manner that an arteriovenous malformation can be sealed off against the blood flow to the extent possible. The same applies to the occlusion of vessels which, for example, are to be separated from the blood circulation system, e.g. because they feed blood to tumors. By appropriately selecting the implant diameter to suit the respective vessel diameter the implant should then be capable of adapting to the relevant vessel diameter. In the area of enlargements and protuberances it shall maximally expand to its nominal diameter.

Furthermore, the present invention also proposes an implant capable of being placed in an atraumatic manner, i.e. without the help of a balloon. Such a placement device must reliably retain the implant until it is finally released from the catheter and, in particular, must also enable the implant to be retracted into the catheter in the event it has not yet been released completely.

As per the invention this objective is reached by providing an implant of the kind first mentioned above with its circular braiding positioned in elongated form and with reduced diameter in an insertion catheter, with the implant expanding at the placement site thus adapting to the vessel diameter and increasing its braiding density.

Suitable materials for the inventive implant are, in particular, those that have a high restoring force or spring action. These are especially materials having superelastic or shape-memory properties, for example nitinol.

In the following description the terms proximal end or distal end of the circular braiding denote, respectively, the end nearest to the attending physician or furthest away from the physician. Accordingly, proximal and distal are to be understood as being nearest to or furthest away from the guide wire of the placement system.

The implants according to the invention are described hereinafter by reference to a circular braiding intended for the sealing off of an aneurysm. It is to be understood that circular braidings of this type may serve a variety of purposes, in particular for the treatment of other types of arteriovenous malformations.

In particular, the implants proposed by the invention are not stents within the usual meaning of the term since they do not have a supporting function. They do not serve to stabilize the vessel wall but are meant to channel the flow of blood in the region of malformations. For example, they shall prevent occlusion means placed in an aneurysm from being flushed out into the vascular pathway. It is to be viewed rather as a kind of in-line element, internal sleeve or flow diverter.

The implants according to the invention are manufactured as circular braiding consisting of a multitude of filaments, with the circular braiding basically forming an endless hose. This endless hose can then be cut to the length desired for the relevant implant. The individual filaments are wound spirally or in the form of a helix, with the individual filaments being intertwined to form a braiding, i.e. crossing one below or above the other. For this purpose, the individual thread filaments are as a rule wound in two directions thus crossing each other at a constant angle, with this angle of intersection being, for example, 90°. According to the invention—and in normal stress-free condition—angles of more than 90° are preferable, especially those ranging between 90 and 160°; and the angles meant here are those which are open towards the ends of the implant. Such a steep and sufficiently dense winding of the individual filaments can produce a circular braiding of high surface density capable of being stretched in axial direction thus yielding significantly smaller diameters. If the stretching forces are omitted and the restoring force of the filament material is sufficiently high the circular braiding again approaches its nominal diameter, i.e. the originally existing stress-free condition, and expands which at the placement site leads to close contact with the vessel wall and causes the mesh structure at the wall to become denser. In particular, this also applies to areas where vessel enlargements exist.

In particular, in such an inventive circular braiding the filament ends projecting at the ends of the implant are joined at least in pairs and connected with each other permanently. This may, for example, be achieved by welding or by a mechanical clasping method and gluing. During this process or additionally the joined filament ends are formed such that they do not cause traumatic effects.

The inventive implants as a rule are not hydraulically expanded and placed in position by means of a balloon. Nonetheless it is necessary to connect the implants to a guide wire in such a manner that they can be reliably controlled. As proposed by the invention this is achieved via connecting elements interacting with a retaining element of the guide wire needed for the placement process. Such connecting elements are the circular braiding's filament ends combined with each other.

Vessel branches (bifurcations) can be taken into account with the inventive implants, for example, in that areas of lower mesh density are provided.

Basically, the circular braiding may be plaited in any known way but in particular are provided as a multi-plaited braid. Especially preferred is a 2-plaited braid. Especially when used in a narrowly plaited arrangement a dense braiding will cause the individual filaments to be highly stressed. However, while a multi-plaited design is conducive to removing stresses from the braid, a too highly plaited arrangement on the other hand will cause the bond in the circular braiding to deteriorate.

In particular, the filaments may also be of multiple folding number. Especially preferred is a folding number 2 or 3 design with two or three filaments each running in parallel. Since during the circular braid manufacturing process the filaments are fed to the process from bobbins two or three filaments are fed from the respective bobbin simultaneously to the mandrel on which the braid is produced.

According to the invention the ends of the filaments are, in particular, connected with each other in pairs, where in the case of multiple filaments 'in pairs' means that in each case two bundles of several filaments are joined. Such bundles may be of compact arrangement in that all wires are combined into a primarily round bundle and the front ends of all wires are fused together so that a uniform dome-shaped end is produced in this way. In this manner a firmly bonded connection of the individual wires is achieved and the bundle end designed so as to be atraumatic.

Alternatively, the wires may be arranged in parallel with their front ends of fan-shaped configuration being fused together. Advantage of this design is the relative small diameter provided in the connection area in comparison to the filament bundling technique.

Another configuration variant is to group the individual filaments in an offset manner, i.e. the wires are cut to length so as to be of staggered arrangement. Via its front end face each wire is connected to the adjacent wire. The longest wire can then be used as connecting element. Such a staggered arrangement may be provided both for a fan-shaped and for a compact configuration of the individual wires.

In any case, the filament ends joined with each other are designed as elements connecting to a retaining element.

As described hereinbefore, important with the stress-free arrangement of the individual filaments in the circular braiding is that the implant surface is designed so as to be as dense as possible. Since braid flexibility must be maintained covering the surface with filaments up to 100% is virtually impossible. Preferred is a surface coverage in the range of 30 to 80%, preferably between 40 and 70%.

To improve the surface coverage the circular braid may be coated with a film consisting, for example, of Teflon, silicone or other biocompatible plastic material. To increase flexibility and expansibility such a plastic film may be provided with slots which are of staggered arrangement, with the longitudinal direction of the slots extending along the peripheral line of the implant. Such a film may, for example, be achieved by immersing the implant into a suitable liquid film medium (dispersion or solution) and subsequent provision of slots, for instance by means of laser equipment. Through immersion the meshes may, for example, be filled fully or partly.

Alternatively, by immersion into a plastic dispersion or solution the individual filaments of the implant may be coated with such a plastic material or the filament cross section increased. In this case the mesh area remains open but the mesh size is significantly reduced.

The implant proposed by the invention is made of customary implant materials having restoring properties, preferably of medical steel having spring characteristic or of a material with shape-memory properties. In the latter case especially nitinol is considered useful.

The implant may be coated in a manner known per se. Suitable coating materials are, in particular, those described for stents, for example materials having antiproliferative, antiphlogistic, antithrombogenous properties or characteristics conducive to ingrowth and/or preventing deposits. Preferred is a coating that promotes the ingrowth of the implant and the formation of neointima. It may be expedient to provide the implant externally with such a type of coating and inside use an agent that inhibits adherence, for example heparin or a derivative thereof, ASA or oligosaccharides and chitin derivatives suitable for the purpose. Further suited in this context are layers of nanoparticles, for example ultra-thin layers of polymeric $SiO_2$ reducing adherence.

In actual practice placement of the inventive implants will be under radiographic control. The implant should therefore be provided with a radiopaque marker material or entirely consist of a radiopaque material. Such radiopaque materials are in particular tantalum, gold, tungsten and platinum metals, for example Pt—Ir alloys, with the latter to be given preference. Such markers may, for instance, be attached as marker elements to the ends of the filaments in a manner known per se or woven into the braid structure of the implant as marker filaments. Individual filaments may as well be coated with a helix consisting of platinum wire or wire of platinum alloys.

According to the invention the filament ends joined with each other are designed so as form connecting elements. As an example, this may be achieved by arranging ball-shaped terminations of defined diameter at these connecting elements, and such terminations may be produced by fusing with the help of laser techniques. Moreover, connecting elements may also be attached by welding/fusing the materials together using a laser. A mechanical bond by means of crimping or the like may also be provided.

Such a connecting element may, exempli gratia, be designed such that a ball-shaped connector is welded to the joined and welded together filament ends, for example via a connecting wire.

Other than a ball shape the design of the connecting elements may also provide for shapes such as anchors, rectangles or other form pieces. At any rate, the connecting elements are intended to function according to the key/lock principle, i.e. they interact with a retaining element being provided over its periphery with suitable recesses or receptacles. As long as the retaining element and the implant attached to it in elongated and diameter-reduced form are moved along within a catheter both are mechanically kept bonded together due to the restraint of the catheter wall; and when the retaining element has exited the catheter the implant expands until it reaches its ultimate diameter and in this way disengages itself from the receptacles provided in the retaining element.

Fixing the implant in the recesses or receptacles of the retaining element may also be brought about by means of a separate hose drawn or placed over the retaining element so as to achieve a form-closed bond with the connecting elements or connectors being in place in the retaining element. When the implant has reached its ultimate position the hose is retracted and in this manner liberates the implant. Following this, the retaining element with guide wire, hose and catheter can be retracted.

Accordingly, the invention also relates to the combination of an implant of the kind described hereinbefore and a guide wire to which the implant is attached via the retaining element.

As mentioned above the combination of retaining element and implant is moved through an endovascular catheter. For this purpose the retaining element has a disk shape and over its periphery is provided with recesses which serve to accommodate the connecting elements of the implant. The diameter of the retaining element is to be selected so that it can be passed without difficulty through a catheter of customary design while the connecting elements however being restrained and kept inside their recesses by the inner wall of the catheter. In this context a ball-shaped design of the connecting elements is thought to be of advantage because the faces contacting the inner wall of a customary catheter and thus friction and resistance of the moving components can be minimized.

As per a preferred embodiment the retaining element consists of two suitably spaced fixing elements which accommodate the implant in stretched form between them. In this case both fixing elements are provided with the respective receptacles for the connecting elements of the implant and the implant has been designed to include suitable connecting elements both on its proximal and its distal end.

A suitably designed retaining element with two fixing elements may have both fixing elements connected to one and the same guide wire and arranged at a defined distance away from each other so that it is ensured the implant of a given length undergoes a defined elongation and tensioning. In this manner any excessive elongation is ruled out and the restoring forces that are exerted after the implant is liberated within the vessel can be fully effective. As an alternative the fixing elements may also be attached to two separate guide wires which enable the implant to be adjusted or elongated by the attending physician or by means of a suitably designed securing device. The second guide wire may also be designed in the form of a guide tube.

BRIEF DESCRIPTION OF THE DRAWINGS

The invention is explained in more detail by way of the enclosed figures where.

DETAILED DESCRIPTION

Figure 1:
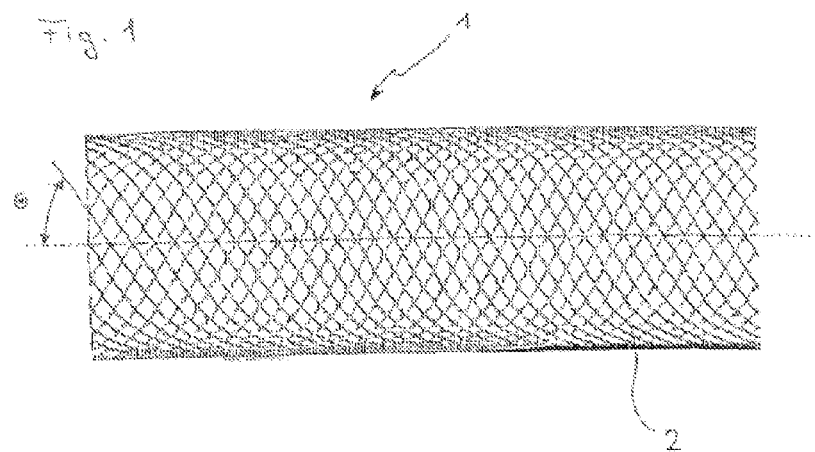
FIG. 1 shows a typical example of a circular braiding as used in the framework of the invention.

FIG. 1 shows the braid structure of an inventive implant 1 consisting of individual filaments 2 intertwined with each other. In the example shown the individual filaments intersect at an angle of approx. 120° with the open side of the angle pointing to the open ends of the circular braiding. The illustration shows the braid in a slightly stretched/elongated state, i.e. the diameter is reduced.

The angle Theta denotes the braid angle in relation to the longitudinal axis, said angle may amount up to 80° in unstretched condition and when nominal diameter has been reached. When the braiding is in elongated position inside the catheter angle Theta may reduce to approx. 7°.

It is to be understood that the nominal diameter of the circular braiding will match the lumen of the target vessel at the location where treatment takes place.

The braid is manufactured on a conventional braiding machine in the form of an endless braid structure. Braiding is performed on a mandrel the external dimensions of which correspond to the inside diameter of the products made on the machine.

The appropriately equipped braiding machine governs the structure of the braid, e.g. the number of threads, the thread run and the number of intersection points over the circumference and per length of lay. The number of threads depends on the number of lace bobbins, with each of said bobbins revolving halfway around the braiding core in both directions.

The filaments usually consist of metal, for example of steel wire, radiopaque platinum metals or platinum alloys or nitinol. However, plastic filaments of sufficient strength may also be used. Ideally, the filament strength amounts to 0.01 to 0.2 mm, in particular ranges between 0.02 and 0.1 mm. To achieve a high coverage of the wall area flat strip material may be used in lieu of wire material, said flat material having, for example, a width ranging between 0.05 and 0.5 mm, preferably up to 0.1 mm, with the above cited strength figures.

The inventive circular braiding may be produced from single filaments (folding number 1) or from two (folding number 2) or more filaments.

Figure 2:
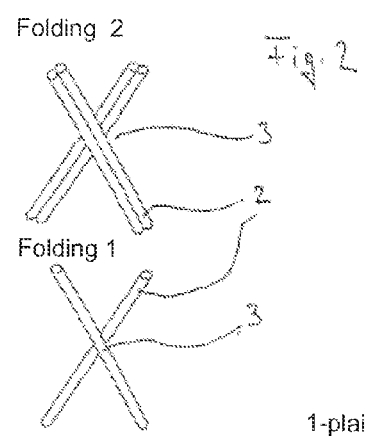
FIG. 2 shows filaments of single or double folding number.

FIG. 2 shows points of intersection 3 where two parallelly guided filaments each cross (folding number 2) or only single filaments 2 intersect (folding number 1). If two or more filaments are put together, these will be fed via the same bobbin.

Figure 3:
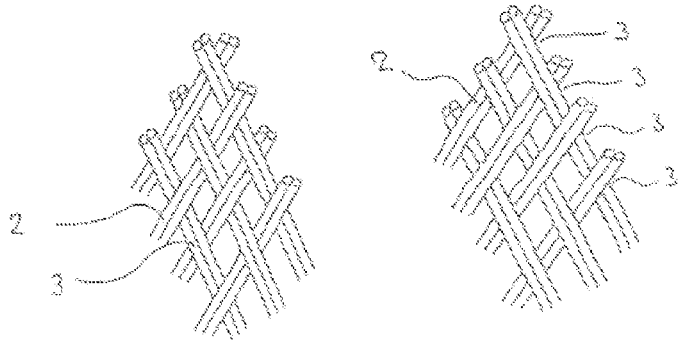
FIG. 3 illustrates a 1-plaited or 2-plaited braiding.

FIG. 3 shows examples of 1-plaited and 2-plaited structures comprising filaments 2 of folding number 2. In the 1-plaited structure the filament pairs are arranged alternating one above the other and one below the other. As can be seen from the illustration, in the 2-plaited structure the filament pairs each are extending above two counter-running filament pairs and then underneath two counter-running filament pairs.

A folding number of two or an even higher folding number results in a higher surface density of the circular braiding and at the same time reduces the longitudinal expansion when the circular braiding is compressed. This higher surface density, however, causes flexibility to diminish, also through increased friction and tension. This may be counteracted by making use of a more highly plaited arrangement, i.e. a 2-plaited or higher-plaited structure will result in higher flexibility. According to the invention, a 2-plaited structure and a folding number of 2 are preferred.

After cutting the product to size to yield specific units the braiding ends have to be properly terminated. This is necessary to ensure the form stability of the braided structure and prevent the vascular system from being injured or damaged. Of equal importance in this respect is to provide an orderly structure of the ends of the circular braiding.

Figure 4A:
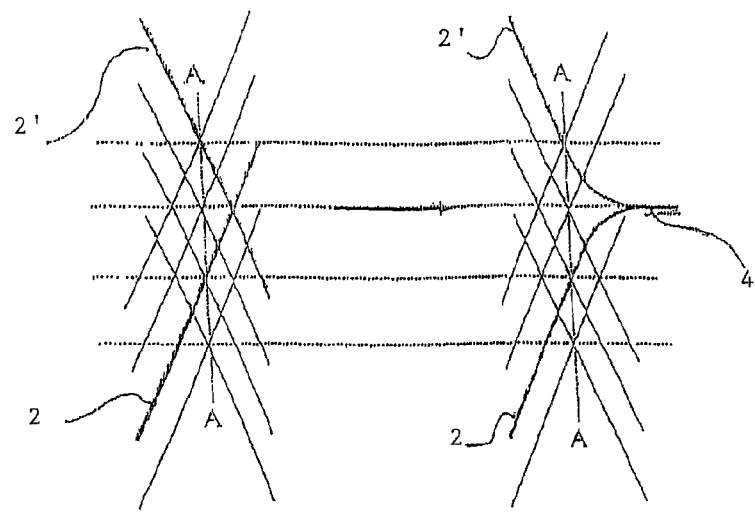
FIG. 4a provides information on how the filament ends of an inventive braiding are joined.

FIG. 4a shows how two filaments 2, 2' are combined at the end of the circular braiding into a filament pair 4, with 2 and 2' being counter-running filaments. For this purpose, the filaments are bent in axial direction and welded together distally. In this case the filaments positioned one above the other at the marginal to points of intersection are connected to each other. Points of intersection are to be found, for example, at locations where the horizontal reference lines cross the vertical nodal plane A-A.

Figure 4B:
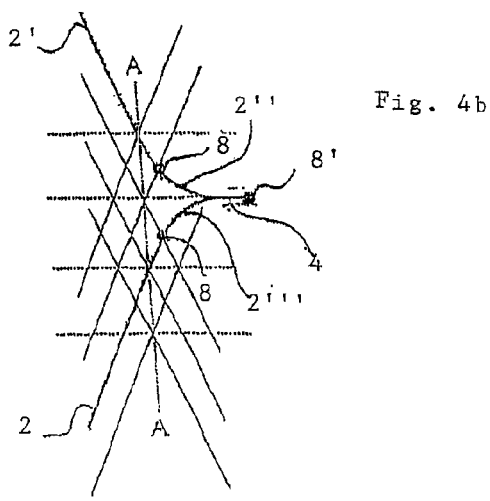
FIG. 4b shows a second variant for the connection of two filament ends.

As can be seen from FIG. 4b there is another variant of joining two filaments 2 and 2' to form a filament pair 4 connected to filaments 2, 2' via two arms 2" and 2"' and welding spots 8. The two arms of the connecting piece 4 are brought together at welding spot 8'. The filament pair 4 can be pre-assembled and makes it possible to achieve a uniform and consistent termination that does not interfere with the arrangement of filaments 2, 2'.

Figure 5:
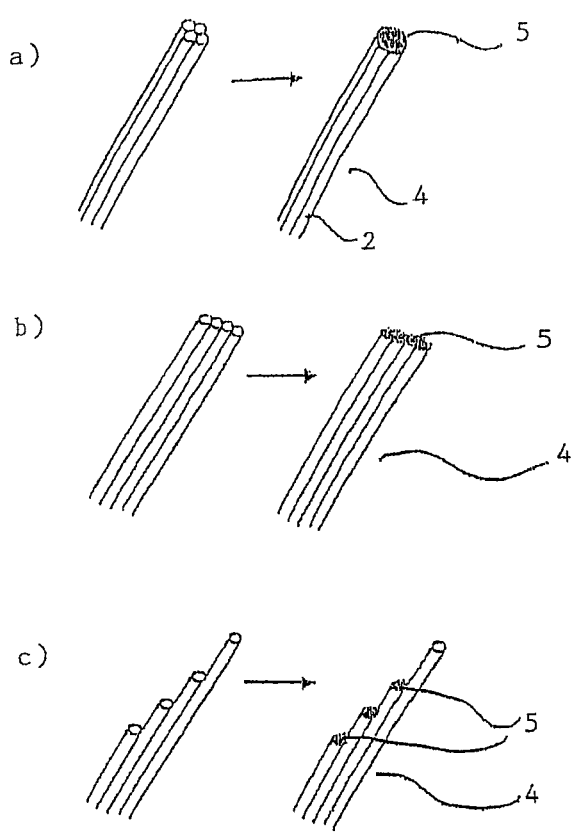
FIG. 5a shows a compact, bundled arrangement of filament ends.
FIG. 5b illustrates joined filament ends of fan-shaped arrangement.
FIG. 5c shows joined filament ends of staggered arrangement.

FIG. 5 shows termination variants for the braiding, as generally described in FIG. 4. As per FIG. 5a a bundle comprises four filaments 2 the front ends of which are welded together, for example by means of a laser welding technique. On the one hand this results in the individual filaments being joined permanently thus preventing the disintegration of the circular braid and at the same time makes sure the otherwise injury-prone filament tips are reshaped so as to be atraumatic. According to a preferred embodiment the welding spots 5 may be designed to form a ball or form piece capable of serving as connecting elements.

FIG. 5b shows a fan-shaped configuration of a filament bundle 4, with the individual filaments being distally connected with each other by means of a common welding spot 5.

In FIG. 5c a staggered arrangement of the individual filament ends of filament bundle 4 is illustrated including the individual welding spots 5 by means of which the connection between the respective filaments is made.

This variant provides for the wires to be cut to length so as to be of staggered arrangement. The longest wire may function as connector and may be provided with a shaped element attached to its tip, for example. Via their front end surface all shorter wires are connected to the neighboring wire by a bonding or fusing method. Of special interest when making use of this particular embodiment is the smaller diameter to be expected in the connection area.

In case of a 2-plaited braid structure of folding number 2 with a total of 16 double threads a total of eight welded connections of the kind illustrated in FIG. 5 (others are conceivable) is produced which serve as eight connecting elements for attaching the implant according to the invention to a retaining element.

Figure 6:
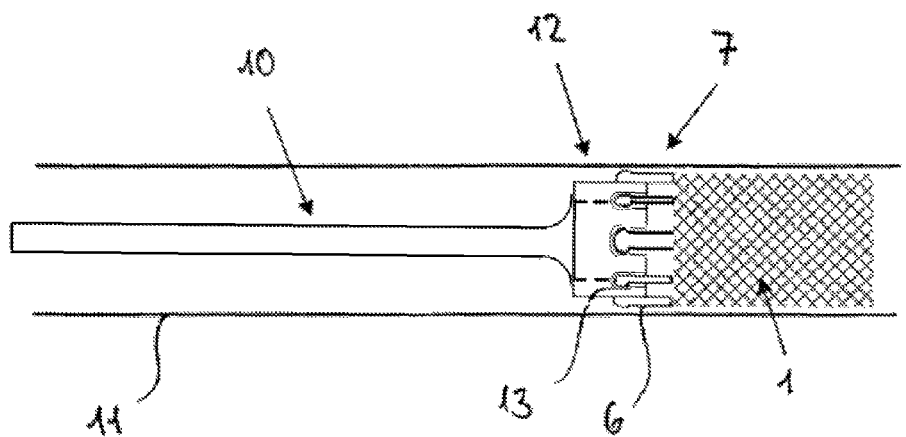
FIG. 6 shows the connection method between guide wire and circular braid by means of a retaining element.

FIG. 6 shows an inventive combination of an implant 1 which is connected via a retaining element 12 to a guide wire 10 and is moved along in a catheter 11. At its proximal end the implant 1 is attached to a retaining element 12 via the terminal filament bundles 7 welded together, said bundles having been reshaped to form connectors 6. Over its periphery the retaining element 12 has been provided with recesses into which the connectors 6 are fitted, said connectors having a kind of ball-shaped tip or head. The retaining element 12 has a disk-shaped cross section and adapts to the inside width of the catheter 11 in such a way that the connectors 6 arranged in recesses 13 are prevented from moving out of the recesses due to the restraining action of the inner catheter wall.

If the implant 1 is moved out of the end of catheter 11 with the aid of the guide wire 10 it is freed and expands causing its diameter to increase. Connectors 6 are now moving out of the recesses 13 causing the implant to be released so that the guide wire and retaining element 12 can be retracted. Expansion of the implant 1 causes it to closely adapt to the wall of the vessel and in this way it is capable of shielding off an arteriovenous malformation such as an aneurysm.

Figure 7:
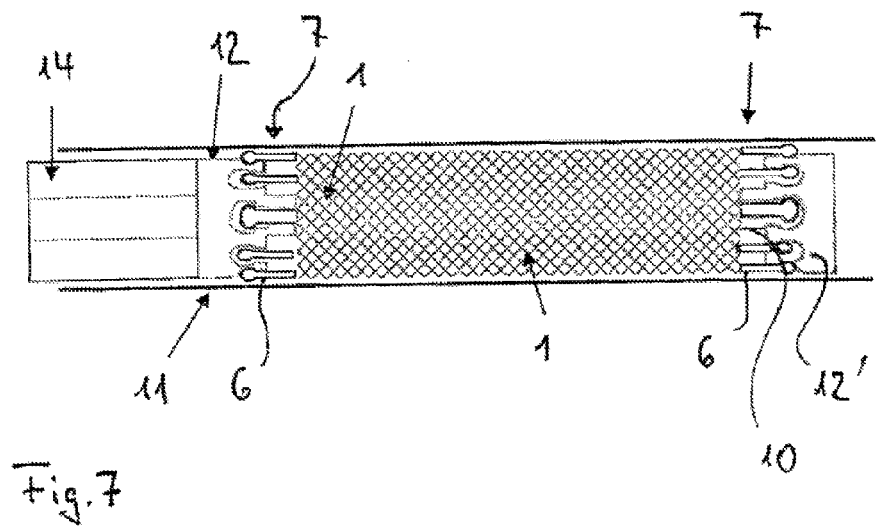
FIG. 7 is an embodiment where two retaining elements are employed.

FIG. 7 shows still another variant of the combination illustrated in FIG. 6 consisting of guide wire, retaining element and implant in a catheter 11. According to this variant it is possible to secure the implant between a proximally located retaining element 12 and a distal retaining element 12'. Both retaining elements 12, 12' are provided with the peripherally arranged recesses into which via the connectors 6 the terminally arranged and welded together filament bundles 7 are inserted. The braiding 1 located in between may be subjected to a varying degree of elongation depending on the spacing of the retaining elements 12, 12' which facilitates movement through the catheter.

To be able to bring about the relative movement two independently operating guiding systems are required. This may, for example, be achieved by providing two separate guide wires 10. In another variant the proximal retaining element 12 is connected to a flexible tube while the distally located retaining element 12' is secured to guide wire 10 extending within this tube. To make sure the system is sufficiently flexible tube 14 and guide wire 10 may be manufactured of nitinol.

Before the implant can be released the system has to be correctly positioned at its distal end. After the system has been released distally the guide wire 10 with the distal retaining element 12' can first be retracted into the catheter 11. Following this, the implant 1 can also be released at its proximal end by retracting the catheter 11 and the proximal retaining element 12 together with tube 14 can be retracted.

Figure 8:
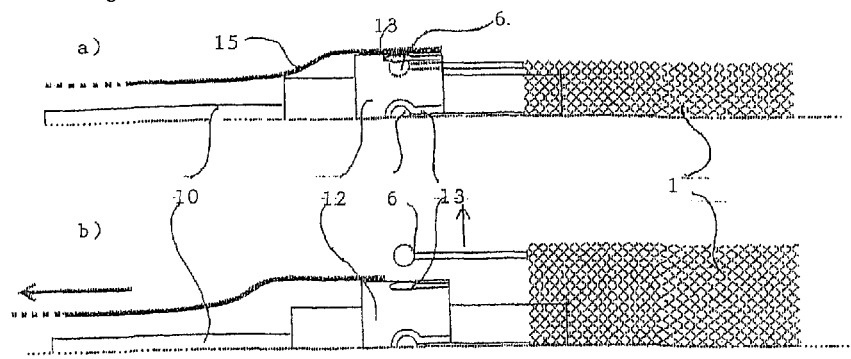
FIG. 8 depicts another variant of attaching an implant to a retaining element using a hose.

The release system according to FIG. 8a shows another variant of an inventive combination of an implant 1 which is connected via a retaining element 12 to a guide wire 10 and is moved along in a catheter which is not illustrated in this figure. At its proximal end the implant 1 is connected to the retaining element 12 via the terminally welded on connectors 6 in such a manner that the connecting balls 6 are fitted into the recesses 13 provided in retaining element 12. Drawn over the retaining element 12 a hose 15 inside which the guide wire 10 extends secures the connectors 6 within the recesses 13.

FIG. 8a shows the combination comprising implant, retaining element, guide wire and hose with secured implant while the implant liberated from the retaining element 12 after the hose 15 has been retracted can be seen in FIG. 8b.

Since the guide wire 10 and the hose 15 can be moved relative to each other within a catheter which has not been illustrated here, the implant can first be appropriately positioned at the placement site following which the catheter is retracted and finally the implant released by retracting the hose 15. Subsequently, hose 15 and guide wire 10 with retaining element 12 can be drawn back into the catheter and removed from the vessel together with the catheter. An implant still retained but already liberated at its distal end may be drawn back into the catheter for a new placement or removal.

Hoses withstanding the required pull forces are known per se. However, to ensure adequate flexibility is achieved even with longer hoses it may be expedient to provide slots or other openings in the hose, primarily in the distal region of the hose. This increases the hose bending quality and makes it possible to displace air from the system before it is applied.

Other variants of this release system are conceivable which may provide, for example, for the connector balls 6 being replaced by connecting elements of some other kind and secured in their position at the retaining element 12 by the catheter 11, a tube 14 or a hose 15.

It is to be understood that the method of fixing an implant to a retaining element as described here by means of a tube, hose or within the catheter may also be employed for other types of implants.

Figure 9:
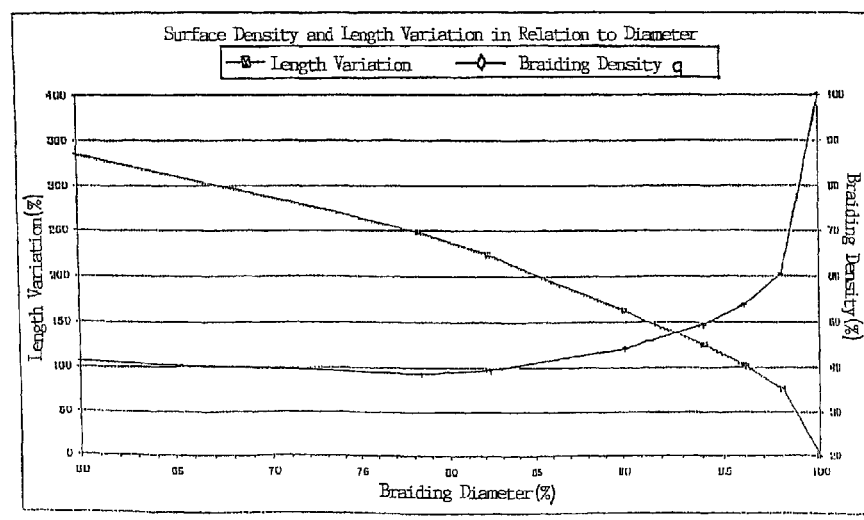
FIG. 9 is a diagram illustrating the correlation between surface density and length variation of an implant according to the invention.

In FIG. 9 a diagram is shown that provides elucidation about the correlation between the surface density and length variation of a braided stent to which the invention relates.

In fully expanded state (static condition) an implant according to the invention having a braid diameter of 100% has a longitudinal expansion of 0%. As the elongation increases the braiding diameter goes down and the braid length doubles with a diameter reduction of 4% and increases in triplicate with a diameter reduction of 15%. This means that an inventive in-line element intended for transportation by a micro-catheter which has to be introduced into the blood vessel near the target site must undergo a significant elongation.

The braid density in this context reaches a value of 100% at full expansion, i.e. with a longitudinal expansion of 0%. The braiding density decreases by 46% when the braid diameter reduces by 4% (longitudinal expansion 100%), and a braid density of 40% is reached when the braid diameter is only 85%.

The diagram shows theoretical values for an ideal cylindrical braiding. It must be taken into account, however, that vessels as a rule are not of ideal cylindrical form and especially in the area of an aneurysm neck where the shielding must take place the vessel diameter, also due to the opening, is often higher in comparison to the adjacent healthy vessel segment. As a result of the malformation characteristics described above the braiding of the in-line implant element is capable of assuming a higher surface density at the desired location and in this manner can impede or block the flow of blood into the aneurysm.

Normally, the surface density/braiding density will be approx. 40 to 70% of the fully expanded state. With well-placed implants according to the invention or when the vessel diameter in the region of an aneurysm is greatly increased values considerably in excess of 70% of the theoretically attainable value may be reached, however.

Figure 10:
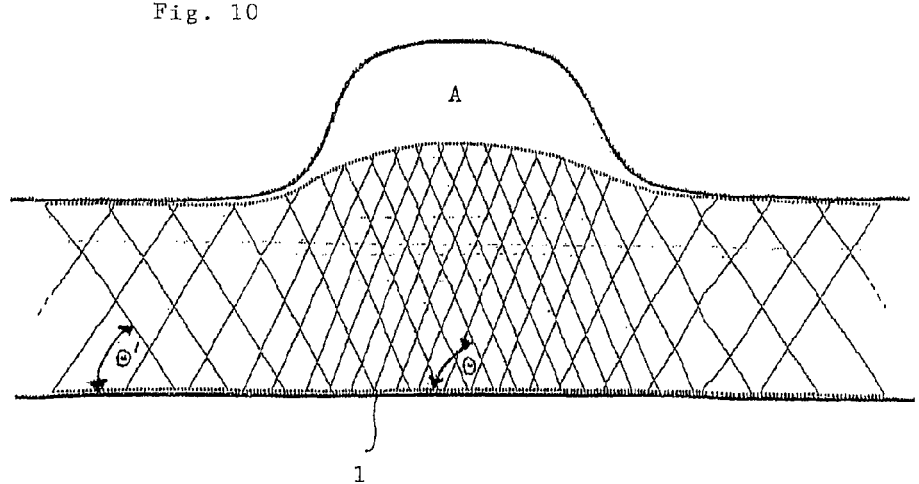
FIG. 10 shows how an inventive implant is arranged in the neck area of an aneurysm.

FIG. 10 is a schematic representation showing an implant according to the invention placed in a vessel in the neck area of an aneurysm A. The major expansion of the braiding 1 occurs in aneurysm area A, with the braid angle Theta being approx. 68°. The filament or braiding density has increased accordingly. In the marginal area of the circular braiding 1 where the vessel lumen is normal the braid angle Theta amounts to 60° causing the filament density to be reduced accordingly.

Due to the filament density being higher in the aneurysm area A the permeability of the inventive circular braiding diminishes which is in line with the intended purpose of channeling the flow of blood in aneurysm region A and "cutting off" the aneurysm A from the blood flow. This isolation or shielding step may, for example, be further enhanced by filling the aneurysm space A external to the implant 1 with an occlusion spiral or other occlusion means.

The invention claimed is:

1. A combination comprising an insertion catheter, an implant, a guide wire and a retaining element, wherein the implant is attached to the guide wire via the retaining element, the implant for blood vessels for influencing blood flow in areas of arteriovenous malformations, said implant having a wall comprising individual filaments combined so as to form a circular braiding, wherein the filaments have ends and said circular braiding being positionable in elongated form and with a reduced diameter in the insertion catheter and expandable at a placement site thus adapting to a vessel diameter and increasing its braiding density, wherein the circular braiding has a proximal end and a distal end, and at the proximal end the filament ends are joined at least in pairs and connected with each other permanently, with the joined filament ends being formed such that they do not cause traumatic effects and forming connecting elements that attach to the retaining element, the retaining element being provided over its periphery with recesses into which the connecting elements are fitted, the combination further comprising a hose drawn over the retaining element in a closed-form way with the connecting elements fitted therein so that the implant is liberated by retraction of the hose, wherein the drawn-over hose is not extendable over the circular braiding, and wherein the circular braiding has a surface coverage in stress-free arrangement achieved by the individual filaments in the range of between 30 and 80%, and the retaining element is secured to the guide wire, the retaining element being retractable into the insertion catheter by retracting the guide wire into the insertion catheter after liberation of the implant.

2. The combination according to claim 1, characterized in that the individual filaments of the circular braiding have shape-memory properties.

3. The combination according to claim 2, characterized in that the individual filaments comprise nitinol.

4. The combination according to claim 1, characterized in that the filament ends are welded to each other.

5. The combination according to claim 1, characterized in that a folding number 2 applies to the filaments.

6. The combination according to claim 1, characterized in that the filament ends are welded to each other so as to be level with each other.

7. The combination according to claim 1, characterized in that the filament ends are welded to each other so as to be of staggered arrangement in length.

8. The combination according to claim 1, characterized in that the surface coverage ranges between 40 and 70%.

9. The combination according to claim 1, characterized in that the individual filaments of the circular braiding are coated with plastic material.

10. The combination according to claim 1, characterized in that the circular braiding is coated with a film or is provided with meshes filled with plastic material in whole or part.

11. The combination according to claim 10, characterized in that the film is provided with slots with a view to increasing the film's expansibility.

12. The combination according to claim 1, characterized in that the implant is provided with at least one radiopaque marker material.

13. The combination according to claim 12, characterized in that the implant contains marker elements.

14. The combination according to claim 13, characterized in that the marker elements are filaments made of platinum or platinum alloys woven into the circular braiding or surrounding the individual filaments of the circular braiding in a form resembling a helix.

15. The combination according to claim 14, characterized in that ball-shaped terminations of defined diameter are arranged at the ends of filaments as the connecting elements.

16. The combination according to claim 15, characterized in that the connecting elements are welded to the filament ends.

17. The combination according to claim 1, characterized in that the retaining element has a disk shape and on its periphery is provided with the recesses serving to accommodate the connecting elements of the implant.

18. The combination according to claim 1, characterized in that the retaining element consists of two suitably spaced fixing elements which accommodate the implant in stretched form between them.

19. The combination according to claim 18, further comprising another guide wire, wherein each guide wire is secured to a different fixing element such that the spacing of the fixing elements relative to each other can be adjusted.

20. The combination according to claim 1, wherein the implant has ends and the circular braiding is of two-plaited design, and wherein the individual filaments comprise counter-running filaments having ends and bent in an axial direction at the implant ends and connected by weld spots provided at the counter-running filament ends, four or more of the counter-running filaments aligned in the axial direction and brought together on a same plane being welded to each other.

21. The combination according to claim 1, wherein the guide wire has a diameter that is less than a diameter of the retaining element.

* * * * *